US011859026B2

United States Patent
Rodrigues et al.

(10) Patent No.: US 11,859,026 B2
(45) Date of Patent: Jan. 2, 2024

(54) WATER SOLUBLE PYRANINE POLYMERS AND METHOD OF MAKING

(71) Applicant: NOURYON CHEMICALS INTERNATIONAL B.V., Arnhem (NL)

(72) Inventors: Klin Aloysius Rodrigues, Signal Mountain, TN (US); Andrew James Bailey, Chattanooga, TN (US); Jobie Lebron Jones, Ringgold, GA (US); Wyatt August Winkenwerder, New Milford, CT (US); Elliot Isaac Band, Pleasantville, NY (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 485 days.

(21) Appl. No.: 16/635,828

(22) PCT Filed: Jul. 27, 2018

(86) PCT No.: PCT/EP2018/070398
§ 371 (c)(1),
(2) Date: Jan. 31, 2020

(87) PCT Pub. No.: WO2019/025305
PCT Pub. Date: Feb. 7, 2019

(65) Prior Publication Data
US 2020/0223959 A1 Jul. 16, 2020

Related U.S. Application Data

(60) Provisional application No. 62/539,901, filed on Aug. 1, 2017.

(30) Foreign Application Priority Data

Oct. 17, 2017 (EP) ..................... 17196930

(51) Int. Cl.
| | |
|---|---|
| C08F 16/30 | (2006.01) |
| C02F 5/10 | (2023.01) |
| C07C 309/43 | (2006.01) |
| C09K 11/06 | (2006.01) |
| C02F 5/12 | (2023.01) |
| C02F 103/02 | (2006.01) |

(52) U.S. Cl.
CPC ............... *C08F 16/30* (2013.01); *C02F 5/10* (2013.01); *C07C 309/43* (2013.01); *C09K 11/06* (2013.01); *C02F 2103/023* (2013.01); *C02F 2303/08* (2013.01); *C07C 2603/50* (2017.05); *C09K 2211/1416* (2013.01)

(58) Field of Classification Search
None
See application file for complete search history.

(56) References Cited

U.S. PATENT DOCUMENTS

| | | | |
|---|---|---|---|
| 5,171,450 A | 12/1992 | Hoots | |
| 5,514,710 A | 5/1996 | Haugland et al. | |
| 5,698,512 A | 12/1997 | Austin et al. | |
| 5,925,610 A | 7/1999 | Austin et al. | |
| 5,986,030 A | 11/1999 | Murray et al. | |
| 6,280,635 B1 | 8/2001 | Moriarty et al. | |
| 6,312,644 B1 * | 11/2001 | Moriarty ............... | C09K 11/06 252/301.16 |
| 7,087,189 B2 | 8/2006 | Austin et al. | |
| 7,666,963 B2 | 2/2010 | Rodrigues et al. | |
| 8,871,880 B2 | 10/2014 | Naumann et al. | |
| 9,109,068 B2 | 8/2015 | Rodrigues et al. | |
| 10,323,112 B2 | 6/2019 | Atkins et al. | |
| 2013/0253158 A1 | 9/2013 | Naumann et al. | |

FOREIGN PATENT DOCUMENTS

| | | |
|---|---|---|
| JP | 9-108696 A | 4/1997 |
| JP | 2003-529553 A | 10/2003 |
| JP | 2015-519409 A | 7/2015 |
| JP | 2016-512996 A | 5/2016 |
| WO | 01/44403 A1 | 6/2001 |
| WO | 2013/139673 A1 | 9/2013 |
| WO | WO-2013139673 A1 * | 9/2013 ............ C08F 220/06 |

OTHER PUBLICATIONS

Synthesis of Sulfonated Aryl Alkyl Ether Monomers in Cost Effective Solvents,ip.com, Jun. 28, 2017.

* cited by examiner

*Primary Examiner* — Clare M Perrin
(74) *Attorney, Agent, or Firm* — Norris McLaughlin, P.A.

(57) ABSTRACT

A method of making a pyranine monomer composition comprises the step of reacting pyranine with a functionalizing agent that functionalizes the pyranine molecule with a polymerizable functional group to provide a composition of functionalized pyranine monomers, said functionalization reaction taking place in an aqueous reaction medium, and in the presence of a molar excess of said functionalizing agent, such that the functionalization reaction product is a monomer composition substantially free of unfunctionalized pyranine compound. The pyranine monomer compositions made by the method can be used to make fluorescent tagged water soluble polymer compositions that advantageously are substantially free of unpolymerized pyranine. The fluorescent tagged water soluble polymer compositions can be used in a method of inhibiting scale in industrial water systems.

20 Claims, No Drawings

WATER SOLUBLE PYRANINE POLYMERS AND METHOD OF MAKING

This application is a 371 of PCT/EP2018/070398, filed Jul. 27, 2018, which claims priority benefit under 35 U.S.C. § 119 of European Patent Application No. 17196930.6 filed Oct. 17, 2017; and U.S. Provisional Patent Application No. 62/539,901, filed Aug. 1, 2017, the disclosures of which are incorporated herein by reference.

FIELD OF THE APPLICATION

This application relates generally to methods of synthesizing pyranine monomers, compositions of pyranine monomers synthesized by the method, and compositions of water soluble polymers made with the pyranine monomer compositions, which compositions of water soluble polymers incorporating pyranine monomers are useful in the treatment of industrial water systems, as well as for scale control in oil field applications.

BACKGROUND

There are many industrial water systems, including, but not limited to, cooling water systems and boiler water systems. Such industrial water systems are subject to corrosion and the formation of scale.

It is known that certain types of water soluble treatment polymers are effective for preventing formation of scale and suppressing the occurrence of corrosion in industrial water systems. These water soluble treatment polymers are known to persons of ordinary skill in the art of industrial water systems and are widely used in scale and corrosion inhibition products. Such water soluble treatment polymers generally exhibit activity against scale and corrosion when added to water in an amount in the range of from about 1 to about 100 milligrams of solid component active per liter of water.

The efficacy of water soluble treatment polymers in inhibiting scale and suppressing corrosion depends in part on the concentration of the water soluble treatment polymer in the water system. Water soluble treatment polymers added to a cooling water system can be consumed by many causes, leading to changes in concentration of the water soluble polymer. Therefore, it is important for the optimum operation of an industrial water system to be able to determine the concentration of water soluble treatment polymers in the water.

It is known that the concentration of water soluble treatment polymers used as components of scale and corrosion inhibitors in industrial water systems can be monitored if the polymer is tagged with a fluorescent monomer. The amount of fluorescent monomer incorporated into the water soluble polymer must be enough so that the fluorescence of the water soluble polymer can be adequately measured, however, it must not be so much as to adversely impact the performance of the water soluble polymer as a treatment agent. Because the concentration of the tagged water soluble treatment polymer can be determined using a fluorimeter, it is also possible to measure consumption of the water soluble treatment polymer directly. It is important to be able to measure consumption directly because consumption of a water soluble treatment polymer usually indicates that a non-desired event, such as scaling, is occurring. Thus by being able to measure consumption of the water soluble polymeric additive, the scaling activity in the cooling system can be monitored. Such systems are disclosed, for example, in U.S. Pat. Nos. 5,171,450, 5,986,030, and 6,280,635. In some systems, such measurements can be conducted in line, in situ, in real time.

Problems with accurate determination of the amount of tagged polymer consumed by scale or other events can arise if free fluorescent compound is present in the tagged polymer composition used for water treatment. This free fluorescent compound will not be consumed when the polymer is consumed in scale control, but will remain suspended in the water system, where it will be detected by the system fluorimeters, leading to an inaccurate understanding of the scale control progress in the system.

In preparing a fluorescent compound to tag a polymer, the fluorescent compound must first be functionalized with a polymerizable moiety, typically a moiety with a carbon-carbon double bond, to form a fluorescent monomer. If a reaction to functionalize a fluorescent compound does not go substantially to completion, then unfunctionalized fluorescent compound can remain in the monomer reaction product. Because the unfunctionalized fluorescent compound and the functionalized fluorescent monomer are chemically very similar, it can be difficult to separate any unfunctionalized fluorescent compound starting material remaining from the monomer reaction product. If this monomer reaction product containing both the desired monomer and the undesirable unfunctionalized fluorescent compound is then added to a polymerization reaction mixture in the polymerization of a water soluble fluorescent tagged polymer, then the unfunctionalized fluorescent compound can also be present in the polymerization reaction product composition. The unfunctionalized fluorescent compound will likewise be difficult to separate from the polymerization reaction product composition.

When a tagged water soluble polymer composition is used to treat an industrial water system, any unfunctionalized free fluorescent compound that is present in the polymer composition will add to the fluorescence signal detected, leading to an inaccurate determination of the amount of fluorescent-tagged water soluble polymer present in the water system. Water in industrial systems is typically recycled, three to five times or even more. With each cycle of use, an additional dose of the fluorescent polymer composition is added, thus multiplying the amount of unfunctionalized fluorescent compound present in the system. After only a few cycles this can significantly adversely affect the accuracy of subsequent measurements of the amount of fluorescent polymer present. Thus it would be desirable to minimize the amount of unfunctionalized free fluorescent compound present in a composition of a water soluble polymer tagged with a fluorescent monomer.

U.S. Pat. No. 6,312,644, incorporated herein by reference, teaches that the fluorescent compound pyranine can be functionalized with either an allyl group or a vinylbenzyl group by reacting the pyranine with either allyl chloride or vinylbenzyl chloride, respectively, added as a single addition to the pyranine in a polar organic solvent such as dimethyl sulfoxide (DMSO). In the method of U.S. Pat. No. 6,312,644, the reaction is conducted under an inert atmosphere, and the organic solvent is distilled off at low pressures. Both of these requirements are difficult and expensive to implement on a commercial scale. Further, the monomer is stated in the examples to be produced in "over 90% yield," which leaves a significant portion of unreacted pyranine in the monomer reaction product.

WO 2013/139673 also discloses the synthesis of fluorescent monomers based on pyranine under an inert atmosphere in DMSO, which monomers are used in the synthesis of water-insoluble superabsorbent polymers with desired optical properties. In the examples, the monomers are prepared by providing pyranine in DMSO, adding an amount of aqueous NaOH, and then adding a functionalizing compound all in one portion.

IP.com document IPCOM000250326D with an electronic publication date of Jun. 28, 2017 states that it discloses the synthesis of sulfonated aryl alkyl ether monomers in cost effective solvents. The publication discloses at pages 3-5 the synthesis of methallyl derivatives of hydroxypyrenetrisulfonic acid sodium salt. When the reaction was conducted in isopropanol, the final reported ratio of unfunctionalized pyranine to functionalized pyranine in the reaction mixture was 1:1.2. When it was attempted to conduct the reaction in a water/isopropanol mixture, the reaction mixture split into two phases when the base was added.

It is desired to provide a method of making a fluorescent monomer composition that contains less than 5 mol % of unfunctionalized fluorescent compound and which method avoids the disadvantages of prior art methods, and particularly the disadvantages associated with methods requiring an inert atmosphere and the use of DMSO.

It is further desired to provide a fluorescent monomer composition which monomer composition contains less than 5 mol % of unfunctionalized fluorescent compound based on the total moles of functionalized fluorescent monomer and unfunctionalized fluorescent compound.

It is further desired to provide a fluorescent-tagged polymer composition, the polymer composition containing less than 5 mol % of unfunctionalized fluorescent compound, based on the total moles of unfunctionalized fluorescent compound, unpolymerized fluorescent monomer, and polymerized fluorescent monomer.

It is further desired to provide a fluorescent-tagged polymer composition that is can provide a more accurate indication of scale inhibition when used in treatment of industrial water systems as compared to fluorescent tagged polymer compositions of the prior art.

The aspects, objects and the several advantages of the compositions and methods disclosed herein will be apparent from the following specification and appended claims.

SUMMARY

This application relates to improved methods of making pyranine monomers, improved pyranine monomer compositions, and improved compositions of pyranine tagged fluorescent polymers and the use thereof.

In one aspect of the disclosure, a method for making a pyranine monomer composition comprises the step of reacting pyranine with a functionalizing agent that functionalizes the pyranine molecule with a polymerizable functional group to provide a composition of functionalized pyranine monomers, the functionalization reaction taking place in an aqueous reaction medium with an excess of the functionalizing agent, and under reaction conditions such that the reaction goes substantially to completion, whereby the functionalization reaction product is a monomer composition containing less than 5 mol % of unfunctionalized pyranine compound based on the total moles of functionalized pyranine monomer and unfunctionalized fluorescent compound.

In one embodiment, a method for making a functionalized pyranine monomer composition comprises the steps of
providing a starting amount of pyranine in an aqueous solvent system,
adding an amount of base to the aqueous solvent system,
dosing to the aqueous solvent system an amount of a polymerizable functionalizing agent to form a reaction mixture, thereby initiating the reaction of the pyranine with the functionalizing agent to functionalize the pyranine molecule with a polymerizable functional group, and
maintaining the dosing of the functionalizing agent to the reaction mixture during the reaction of the pyranine with the functionalizing agent until the amount of functionalizing agent dosed to the system exceeds the starting amount of pyranine on a molar basis.

In one embodiment, a method for making a functionalized pyranine monomer composition comprises the steps of
providing a starting amount of pyranine in an aqueous solvent system,
adding an amount of base to the aqueous solvent system,
dosing to the aqueous solvent system an amount of a polymerizable functionalizing agent to form a reaction mixture, thereby initiating the reaction of the pyranine with the functionalizing agent to functionalize the pyranine molecule with a polymerizable functional group,
maintaining the dosing of the functionalizing agent to the reaction mixture during the reaction of the pyranine with the functionalizing agent until the amount of functionalizing agent dosed to the system exceeds the starting amount of pyranine on a molar basis, and
continuing the reaction of pyranine with the functionalizing agent until at least 95 mol % of the starting amount of pyranine has been functionalized with the functionalizing agent.

In one embodiment, the base is added to the solvent system prior to the addition of the functionalizing agent.

In one embodiment the step of adding the base is accomplished by the simultaneous dosing of the base and the functionalizing agent to the aqueous solvent system, with the dosing of both the functionalizing agent and the base being maintained during the reaction of the pyranine with the functionalizing agent until the amount of functionalizing agent dosed to the system exceeds the starting amount of pyranine on a molar basis.

In one embodiment of this aspect of the disclosure, the aqueous reaction medium optionally comprises one or more water-soluble organic co-solvents. In one aspect the one or more water-soluble organic co-solvents are selected from the group consisting of $C_1$-$C_6$ alcohols. In one embodiment the co-solvent is selected from methanol, ethanol, n-propanol, and isopropanol. In one embodiment the co-solvent is selected from methanol and n-propanol. In one embodiment the co-solvent is n-propanol.

In one embodiment the method of the disclosure is carried out over a time period of from about five minutes to about 24 hours; in one embodiment from about 30 minutes to about 18 hours, in one embodiment from about 1 hour to about ten hours.

Following the dosing method of the disclosure herein can result in at least 95 mol % of the starting amount of pyranine being functionalized with the functionalizing agent; as compared to a much lower functionalization rate obtained when all the reactants are added to the solvent system in a single shot.

In one embodiment of the method of the disclosure the functionalizing agent is a compound of the formula (I)

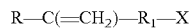

(I)

wherein

R₁ is selected from optionally substituted —$C_1$-$C_{10}$alkyl-, -aryl-$C_1$-$C_{10}$alkyl-, —C(O)—, —$CH_2$NH—C(O)—, and —C($CH_3$)$_2$—NH—C(O)—, R is H or optionally substituted $C_1$-$C_{10}$ alkyl-, and X is a leaving group.

Reaction of a functionalizing agent of formula (I) with pyranine in accordance with the disclosed method yields a monomer composition comprising pyranine monomer of formula (IIa):

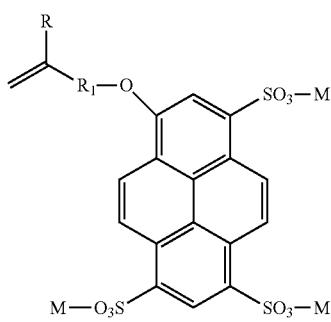

(IIa)

wherein M is selected from the group consisting of hydrogen, sodium, potassium, cesium, rubidium, lithium, ammonium, tetraalkylammonium and R₁ is selected from optionally substituted —$C_1$-$C_{10}$alkyl-, -aryl-$C_1$-$C_{10}$alkyl-, —C(O)—, —$CH_2$NH—C(O)—, and —C($CH_3$)$_2$—NH—C(O)—, and R is H or optionally substituted $C_1$-$C_{10}$alkyl-, the monomer composition containing less than 5 mol % of unfunctionalized pyranine compound based on the total moles of functionalized and unfunctionalized fluorescent compound in the composition.

In one embodiment of this aspect of the disclosure, the monomer composition comprises a pyranine monomer functionalized with a methallyl group.

Yet another aspect of the disclosure is a polymer composition comprising a fluorescent tagged water soluble polymer polymerized with the reaction product of the pyranine functionalization reaction disclosed herein, said polymer composition containing less than 5 mol % of unfunctionalized fluorescent compound, based on the total moles of unfunctionalized fluorescent compound, unpolymerized fluorescent monomer, and polymerized fluorescent monomer.

DETAILED DESCRIPTION

In this application, a monomer composition of functionalized pyranine monomer being "substantially free" of unfunctionalized pyranine compound means that the monomer composition comprises less than 5 mol % of unfunctionalized pyranine compound, or less than 4 mol %, or less than 3 mol %, or less than 2 mol %, or less than 1 mol %, or less than 0.5 mol %, based on the total moles of the unfunctionalized pyranine compound and functionalized pyranine monomer in the monomer composition.

In this application, a polymer composition of a water soluble fluorescent tagged polymer being "substantially free" of unpolymerized pyranine means that the composition comprises less than 5 mol %, or less than 4 mol %, or less than 3 mol %, or less than 2 mol %, or less than 1 mol %, or less than 0.5 mol %, of total unpolymerized pyranine, based on the moles of total pyranine in the composition. The "total unpolymerized pyranine" in the polymer composition is the sum of the unfunctionalized pyranine compound and unpolymerized pyranine monomer that is not polymerized into the polymer. The "total pyranine" in the polymer composition is the sum of the total unpolymerized pyranine and the pyranine monomer that is polymerized into the polymer.

In this application, the term "water-soluble polymer" means that the polymer has a solubility in water of at least 1 g/L, or preferably at least 10 g/L, or more preferably at least 100 g/L, when measured in an aqueous composition having a pH of 7 at a temperature of 25° C.

In this application, the term "water-soluble organic co-solvent" means that the co-solvent has a solubility in water of at least 20 g/L, or preferably at least 50 g/L, or more preferably at least 70 g/L, when measured in an aqueous composition having a pH of 7 at a temperature of 25° C.

In this application, the term "dosing" of a reactant into a reaction mixture means that the reactant is added over a period of time during the course of the reaction, as opposed to a single addition of an entire reactant portion.

The present application is based upon the discovery that pyranine can be reacted with a functionalizing agent to provide a pyranine monomer having a polymerizable functional group, the reaction taking place in an aqueous system with an excess of the functionalizing agent, under conditions such that the reaction goes substantially to completion, thereby providing a monomer composition of functionalized polymerizable pyranine monomers, the composition containing less than 5 mol % of unfunctionalized pyranine compound based on the total moles of functionalized pyranine monomer and unfunctionalized fluorescent compound. These compositions of functionalized pyranine monomers are useful in the preparation of water soluble fluorescent tagged polymers that can be used as treatment polymers in industrial water systems, and as scale-control polymers in oilfield applications.

In one embodiment, a method for making a functionalized pyranine monomer composition comprises the steps of providing a starting amount of pyranine in an aqueous solvent system, adding an amount of base to the aqueous solvent system, dosing to the aqueous solvent system an amount of a polymerizable functionalizing agent to form a reaction mixture, thereby initiating the reaction of the pyranine with the functionalizing agent to functionalize the pyranine molecule with a polymerizable functional group, and maintaining the dosing of the functionalizing agent to the reaction mixture during the reaction of the pyranine with the functionalizing agent until the amount of functionalizing agent dosed to the system exceeds the starting amount of pyranine on a molar basis.

In one embodiment, a method for making a functionalized pyranine monomer composition comprises the steps of providing a starting amount of pyranine in an aqueous solvent system, adding an amount of base to the aqueous solvent system, dosing to the aqueous solvent system an amount of a polymerizable functionalizing agent to form a reaction mixture, thereby initiating the reaction of the pyranine with the functionalizing agent to functionalize the pyranine molecule with a polymerizable functional group, maintaining the dosing of the functionalizing agent to the reaction mixture during the reaction of the pyranine with the functionalizing agent until the amount of functionalizing agent dosed to the system exceeds the starting amount of pyranine on a molar basis, and continuing the reaction of pyranine with the functionalizing agent until at least 95 mol % of the starting amount of pyranine has been functionalized with the functionalizing agent.

In one embodiment, the base is added to the solvent system prior to the dosing of the functionalizing agent.

In one embodiment the step of adding the base is accomplished by the simultaneous dosing of the base and the functionalizing agent to the aqueously solvent system, with the dosing of both the functionalizing agent and the base being maintained during the reaction of the pyranine with the functionalizing agent until the amount of functionalizing agent dosed to the system exceeds the starting amount of pyranine on a molar basis.

In one embodiment, the dosing of base to the reaction mixture continues after the addition of the functionalizing agent is complete and during the continued reaction of the pyranine with the functionalizing agent.

In one embodiment the method of the disclosure is carried out over a time period of from about five minutes to about 24 hours; in one embodiment from about 30 minutes to about 18 hours, in one embodiment from about 1 hour to about ten hours.

To optimize the conversion of unfunctionalized pyranine compound to functionalized pyranine monomer, it is preferred that the functionalizing agent and the base each be dosed slowly into the reaction mixture. In one embodiment, the functionalizing agent can be added at a rate of no more than 50% of the total dosage amount per hour, or no more than 40% of the total dosage amount per hour, or no more than 30% of the total dosage amount per hour, or no more than 25% of the total dosage amount per hour, or no more than 20% of the total dosage amount per hour, or no more than 15% of the total dosage amount per hour, or no more than 10% of the total dosage amount per hour. The base is dosed to the reaction mixture at a rate no faster than the rate of the dosage of the functionalizing agent, based on the total dosage amount of base.

Following the dosing method of the disclosure herein can result in at least 95 mol % of the starting amount of pyranine being functionalized with the functionalizing agent; as compared to a much lower functionalization rate obtained when all the reactants are added to the solvent system in a single shot.

The skilled artisan will adjust the dosage rates and time of the reaction to achieve optimum functionalization of the pyranine based on the disclosure herein, taking into consideration the quantity of reactants, and the capacity and features of the reaction vessel and dosing apparatus used for each use of the disclosed method.

In one embodiment, the reaction mixture is heated during the step of dosing of the reactants. The heating may be continued during the step of maintaining the reaction until at least 95 mol % of the starting amount of pyranine has been functionalized with the functionalizing agent. In one embodiment the reaction may be terminated by discontinuing the heating of the reaction mixture. In one embodiment, if a co-solvent is used as discussed below, the reaction may be terminated by distilling the co-solvent. The reaction temperature can be at least 50° C., or at least 60° C., or at least 70° C., or at least 80° C. In one embodiment the reaction temperature is in the range of 70-75° C.

In one embodiment of the method the aqueous reaction medium optionally comprises one or more water-soluble organic co-solvents. In one embodiment the one or more water-soluble organic co-solvents are selected from the group consisting of $C_1$-$C_6$ alcohols. In one embodiment the organic co-solvent is selected from the group consisting of methanol, ethanol, n-propanol and isopropanol. In one embodiment of the method the organic co-solvent is selected from one or more of methanol, n-propanol, and isopropanol. In one embodiment of the method the organic co-solvent is selected from one or more of methanol and n-propanol. In one embodiment the water-soluble organic co-solvent is n-propanol. In some embodiments the alcohol co-solvent has unlimited solubility in water.

When a water soluble organic co-solvent is used, the ratio of water to total organic co-solvent on a volume:volume basis is in the range of 20:1-1:20, or in the range of 10:1-1:10, or in the range of 5:1-1:5, or in the range of 4:1-1:4, or in the range of 3:1-1:3.

In one embodiment of the method the polymerizable functional group comprises a carbon-carbon double bond, and the functionalizing agent can be a compound containing such a carbon-carbon double bond, which compound reacts with the hydroxyl group on the pyranine to functionalize the pyranine compound with the carbon-carbon double bond, thereby creating a polymerizable pyranine monomer.

In one embodiment of the method, the functionalizing agent is a compound of the formula (I)

$$R-C(=CH_2)-R_1-X \quad \quad (I)$$

wherein $R_1$ is selected from optionally substituted —$C_1$-$C_{10}$alkyl-, -aryl-$C_1$-$C_{10}$alkyl-, —C(O)—, —$CH_2NH$—C(O)—, —$C(CH_3)_2$—NH—C(O)—, R is H or optionally substituted $C_1$-$C_{10}$alkyl-, and X is a leaving group.

In one embodiment of the method, $R_1$ is selected from —$C_1$-$C_{10}$alkyl- and -aryl-$C_1$-$C_{10}$alkyl-, or —$C_1$-$C_6$alkyl- and -aryl-$C_1$-$C_6$alkyl-, or —$C_1$-$C_3$alkyl- and -aryl-$C_1$-$C_3$alkyl-. In one embodiment $R_1$ is methylene. In one embodiment $R_1$ is benzyl.

In one embodiment R is H or $C_1$-$C_{10}$alkyl-. In one embodiment R is H or $C_1$-$C_6$alkyl-. In one embodiment R is H. In one embodiment R is $C_{1-3}$alkyl-. In one embodiment R is methyl. In one embodiment R is H.

The leaving group X is a moiety that will chemically separate from the R—C(=$CH_2$)—$R_1$— moiety when the functionalizing agent is present in the functionalization reaction system. In one embodiment X is a halide ion. In one embodiment X is chloride. In one embodiment X is —O—C(O)C($CH_3$)=$CH_2$. Other suitable leaving groups include —$SO_2C_6H_4CH_3$ and —$SO_2CH_3$.

In one aspect, a monomer composition comprises a pyranine monomer of formula (IIa):

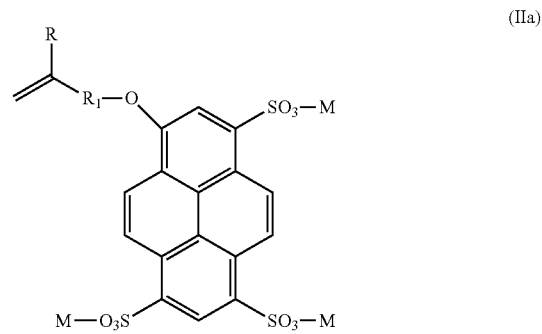

wherein M is selected from the group consisting of hydrogen, sodium, potassium, cesium, rubidium, lithium, ammonium, tetralkylammonium, and $R_1$ is selected from optionally substituted —$C_1$-$C_{10}$alkyl-, -aryl-$C_2$-$C_{10}$alkyl-, —C(O)—, —$CH_2$NH—C(O)—, and —$C(CH_3)_2$—NH—C(O)—, and R is H or optionally substituted $C_1$-$C_{10}$alkyl-;

and wherein the monomer composition comprises less than 5 mol % of unfunctionalized pyranine compound based on the total moles of the unfunctionalized pyranine and pyranine monomer in the monomer composition.

In one embodiment, where M is tetraalkylammonium, the alkyl groups on the ammonium ion are independently selected from linear or branched $C_1$-$C_4$alkyl. In one embodiment, M is tetramethylammonium.

In one aspect the monomer composition comprises less than 4 mol %, or less than 3 mol %, or less than 2 mol %, or less than 1 mol %, or less than 0.5 mol % of unfunctionalized pyranine compound, based on the total moles of the unfunctionalized pyranine and pyranine monomer in the monomer composition.

Preferably M is selected from the group consisting of hydrogen, sodium and potassium. More preferably, M is selected from the group consisting of sodium and potassium.

In an embodiment wherein $R_1$ is —$CH_2$— and R is —$CH_3$, the polymerizable functional group is methallyl, and the methallyl-functionalized pyranine monomers include those selected from the group consisting of compounds of the formula (III):

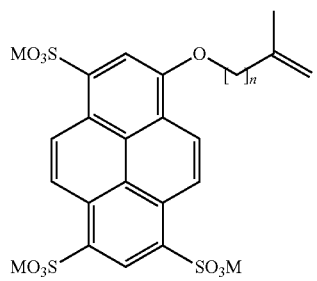

(III)

wherein M is selected from the group consisting of hydrogen, sodium, potassium, cesium, rubidium, lithium, ammonium, and tetralkylammonium, and n is 1.

In formula (IIa) above, the pyranine molecule is functionalized through the pendant hydroxyl group to form an alkoxylated molecule. In some embodiments, some of the pyranine molecules can be functionalized directly on the pyrene ring structure to form an alkylated molecule, illustrated in formula (IIb):

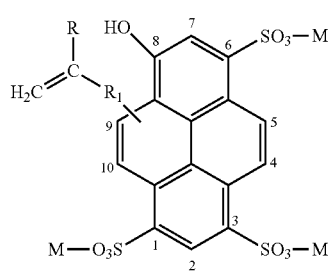

(IIb)

where M is selected from any of hydrogen, sodium, potassium, cesium, rubidium, lithium, ammonium, and tetralkylammonium. Those skilled in the art will recognize that the alkylation can take place at any of the carbon atoms at locations 2, 4, 5, 7, 9 or 10 as illustrated in formula (IIb).

Both the alkoxylated reaction product of formula (IIa) and the alkylated reaction product of formula (IIb) will be polymerizable monomers that can be included in a mixture of monomers to be polymerized in a subsequent polymerization reaction to form water soluble fluorescent tagged polymers.

Representative suitable fluorescent pyranine monomers made by the method of the disclosure herein include without limitation those selected from the group consisting of 8-(methallyloxy)-1,3,6-pyrene trisulfonic acid, methallyl-8-(hydroxy)-1,3,6-pyrene trisulfonic acid, 8-(allyloxy)-1,3,6-pyrene trisulfonic acid, vinyl benzyl-8-(hydroxy)-1,3,6-pyrene trisulfonic acid, allyl-8-(hydroxy)-1,3,6-pyrene trisulfonic acid, 2-(methallyl)-1,3,6-pyrene trisulfonic acid, 4-(methallyl)-1,3,6-pyrene trisulfonic acid, 5-(methallyl)-1,3,6-pyrene trisulfonic acid, 7-(methallyl)-1,3,6-pyrene trisulfonic acid; 9-(methallyl)-1,3,6-pyrene trisulfonic acid; 10-(methallyl)-1,3,6-pyrene trisulfonic acid; 2-(allyl)-1,3,6-pyrene trisulfonic acid, 4-(allyl)-1,3,6-pyrene trisulfonic acid, 5-(allyl)-1,3,6-pyrene trisulfonic acid, 7-(allyl)-1,3,6-pyrene trisulfonic acid; 9-(allyl)-1,3,6-pyrene trisulfonic acid; 10-(allyl)-1,3,6-pyrene trisulfonic acid, 2-vinyl benzyl-1,3,6-pyrene trisulfonic acid, 4-vinyl benzyl-1,3,6-pyrene trisulfonic acid, 5-vinyl benzyl-1,3,6-pyrene trisulfonic acid, 7-vinyl benzyl-1,3,6-pyrene trisulfonic acid, 9-vinyl benzyl-1,3,6-pyrene trisulfonic acid, 10 benzyl-1,3,6-pyrene trisulfonic acid; 8-(3-vinyl benzyloxy)-1,3,6-pyrene trisulfonic acid; 8-(4-vinyl benzyloxy)-1,3,6-pyrene trisulfonic acid; and the sodium, potassium, cesium, rubidium, lithium, ammonium, and tetralkylammonium salts of any of the foregoing.

Representative functionalizing agents suitable for use in the reaction to make fluorescent monomers by the method disclosed herein include without limitation allyl chloride, vinyl benzyl chloride, methacrylic anhydride, allyl isocyanate, 3-isopropenyl-α,α-dimethylbenzyl isocyanate (m-TMI available from Allnex USA Inc., Alpharetta, Ga.), maleic anhydride, itaconic anhydride, (meth) acryloyl chloride, methallyl chloride (or methallyl bromide) for n=1; 4-bromo-1-butene, for n=2; 5-bromo-1-pentene, for n=3; 6-bromo-1-hexene, for n=4; 8-bromo-1-octene, for n=6; and 11-bromo-1-undecene, for n=9. 4-bromo-1-butene-2-methyl, for n=2; 5-bromo-1-pentene-2-methyl, for n=3; 6-bromo-1-hexene-2-methyl, for n=4; 8-bromo-1-octene-2-methyl, for n=6; and 11-bromo-1-undecene-2-methyl, for n=9. At least some of these functionalizing agents are available from Sigma-Aldrich Corp., St. Louis, Mo.

The base is a strong base such as sodium hydroxide, and is used in a stoichiometric amount to deprotonate the hydroxyl group on the pyranine molecule.

An excess of functionalizing agent is used to ensure substantially complete conversion of the pyranine to the desired functionalized polymerizable monomer. In one embodiment the functionalizing agent is present in at least 10% molar excess, in one embodiment at least 50% molar excess, in one embodiment at least 100% molar excess, relative to the starting amount of pyranine.

When an excess of the functionalizing agent of the formula R—C(=$CH_2$)—$R_1$—X is reacted with pyranine in an aqueous medium in the presence of the base, the excess functionalizing agent will react in a side reaction with the base to form an alcohol of the formula R—C(=$CH_2$)—$R_1$—OH as a reaction byproduct. This side reaction also will occur if too great an excess of sodium hydroxide is introduced initially.

Slow addition of the functionalizing agent to the reaction mixture optimizes the reaction of the functionalizing agent with the pyranine compound and minimizes the side reactions that produce byproducts, such as the R—C(=CH$_2$)—R$_1$—OH alcohol.

Addition of the deprotonating base and the functionalizing agent to the pyranine reaction mixture in concurrent streams over an extended period also minimizes unwanted side reactions.

Advantageously, the reaction can be accomplished in an aqueous reaction medium, as discussed above.

It is a further advantage that the functionalization reaction can be carried out under ambient atmosphere, and no inert atmosphere or pressurized vessels are required.

Optionally, the reaction mixture can be heated to further ensure substantially complete functionalization of the pyranine compound. Higher reaction temperatures can be used to shorten the reaction time and drive the reaction further to completion. Generally the reaction is carried out at a temperature in the range of about 20° C. to about 80° C. for a period of time in the range of about 3 to about 10 hours.

For the representative embodiment in which the functionalizing agent is methallyl chloride, the functionalization reaction can be illustrated as Reaction of Pyranine with Methally Chloride

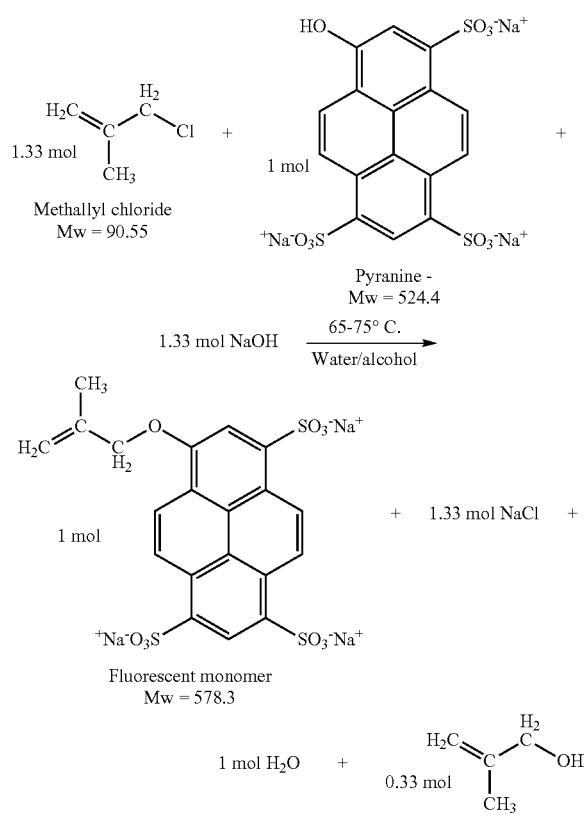

While the reaction product is illustrated above as including only the alkoxylated monomer of formula (IIa), it will be understood that the reaction product also may include a portion of the alkylated monomer of formula (IIb).

Advantageously, this reaction product, including functionalized pyranine monomers, water, co-solvent, and byproducts can be used directly in the polymerization process without a separate isolation step. It is a feature of the disclosed method that any unreacted functionalizing agent or any alcohol byproduct, both of which contain double bonds, can be polymerized into the water treatment polymer with no adverse effects on the properties or effectiveness thereof. In some instances the presence of the unreacted functionalizing agent and alcohol byproduct as co-monomers in the water treatment polymer can also improve the properties or effectiveness of the water treatment polymer. If no isolation step is used then it is preferred that the co-solvent be selected from either methanol or n-propanol, as these co-solvents will not act as a chain transfer agent in the subsequent polymerization reaction and therefore will not affect the molecular weight of the polymer product. In embodiments in which the subsequent polymerization reaction is conducted in the presence of isopropanol, then isopropanol can be used as a co-solvent in the functionalization reaction of the pyranine monomer.

Alternatively, some or all of the water and optional co-solvent can be removed such as by evaporation or distillation, and the desired functionalized monomer reaction product is collected as a solid.

It is a feature of the present application that the functionalization reaction is driven substantially to completion, to minimize the amount of unfunctionalized pyranine present in the monomer reaction product composition and ultimately in the water treatment polymer composition.

After preparation and optional isolation of the fluorescent monomer, fluorescent-tagged water soluble polymers containing these fluorescent monomers can be prepared by inclusion of the fluorescent monomer reaction product into a water soluble polymer.

The amount of fluorescent monomer that is used should be an amount sufficient to allow the water soluble polymer to be detected in the aqueous environment that it is used. The minimum amount of fluorescent moiety that can be used is that amount which gives a signal-to-noise ratio (S/N) of 3 at the desired polymer dosage. The signal-to-noise ratio is that value where the magnitude of the transduced signal (including but not limited to electronic and optical signals) due to the presence of a target analyte in a measurement device is greater than or equal to a level three (3) times the magnitude of a transduced signal where the analyte (species) of interest is not present in the measurement device.

The amount of fluorescent monomer in the tagged polymers is in the range of from about 0.01 wt. % to about 10.0 wt. %, preferably from about 0.05 wt. % to about 2 wt. %, and most preferably from about 0.1 wt. % to about 1.0 wt. %. (When mol percentages are given in this patent application it is understood that these are calculated mol percentages, not measured.)

The amount of the fluorescent monomer will be sufficient to allow the fluorescence to be detected without hindering the scale-inhibition or other desired function of the polymer.

The water soluble polymer further comprises one, two, three or more additional monomers.

In one aspect of the disclosure the other monomers of the water soluble polymer can be selected from one or more of the group consisting of acrylic acid and salts, methacrylic acid and salts, maleic acid and salts, maleic anhydride, acrylamide, crotonic acid and salts; in one aspect the water soluble polymer can additionally include one or more monomers selected from the group consisting of methacrylic acid and salts, maleic acid and salts, maleic anhydride, crotonic acid and salts, itaconic acid and salts, acrylamide, methacrylamide, 2-acrylamido-2-methylpropanesulfonic acid and salts, sodium (meth)allyl sulfonate, allyloxybenzene sulfonic acid and its salts, polyethylene glycol monomethacrylate, vinyl phosphoric acid and salts, styrene sulfonic acid and salts, vinyl sulfonic acid and salts, 3-allyloxy-2-hydroxypropane sulfonic acid and salts, N-alkyl (meth)acrylamide, t-butyl (meth)acrylate, N-alkyl (meth)acrylate, N-alkanol-N-alkyl(meth)acrylate, vinyl acetate, 2-N-alkyl(meth)acrylate, alkyl vinyl ether, alkoxyethyl acrylate, N-alkanol (meth)acrylamide, N,N-dialkyl(meth)acrylamide and 1-vinyl-2-pyrrolidinone; in one aspect the water soluble polymer can additionally include one or more monomers selected from the group consisting of sulfomethylacrylamide and sulfoethylacrylamide.

In one embodiment, the water soluble polymer comprises the fluorescent monomer; maleate monomer; a monomer selected from the group consisting of acrylic acid, methacrylic acid and 2-ethylacrylicacid, and combinations thereof; and a nitrogen-containing, nonionic comonomer selected from the group consisting of acrylamide, methacrylamide, ethylacrylamide, propylacrylamide, isopropylacrylamide, N,N-dimethylacrylamide, N,N-diethylacrylamide, N,N-dipropylacrylamide, N-methylolacrylamide and t-butylacrylamide. In one embodiment, the water soluble polymer is a maleate copolymer comprising about 50 mole percent of maleate monomer, about 40 to about 50 mole percent of a monomer selected from acrylic acid, methacrylic acid and 2-ethylacrylicacid, and combinations thereof, about 1 to about 10 mole percent of the nitrogen-containing, nonionic comonomer; and about 0.05 to about 1 mole percent of the fluorescent monomer. In one embodiment the water soluble polymer is a polymer disclosed in U.S. Pat. No. 5,925,610 and references cited therein, incorporated herein by reference in their entirety, with the addition of a fluorescent monomer as described herein.

In one embodiment, the water soluble polymer comprises the fluorescent monomer, an allyloxybenzenesulfonic acid monomer, a methallyl sulfonic acid monomer, a copolymerizable olefinically unsaturated carboxylic acid monomer and a copolymerizable nonionic monomer. In one embodiment, the water soluble polymer comprises at least about 2.5 mol % of allyloxybenzenesulfonic acid monomer, at least about 0.5 mol % of a methallyl sulfonic add monomer, about 10-20 mol % of a copolymerizable olefinically unsaturated carboxylic acid monomer, about 60-97 mol % of a copolymerizable nonionic monomer, and about 0.05 to about 1 mole percent of the fluorescent monomer. In one embodiment the water soluble polymer is a polymer disclosed in U.S. Pat. No. 5,698,512 and references cited therein, incorporated herein by reference in their entirety, with the addition of a fluorescent monomer as described herein.

In one embodiment, the water-soluble polymer comprises the fluorescent monomer as disclosed herein, a dicarboxylic acid monomer, a monocarboxylic acid monomer, a non-ionic monomer, and sulfonated or sulfated monomer or combinations thereof. In one embodiment the dicarboxylic acid monomer is selected from itaconic acid, maleic acid, maleic anhydride, citraconic acid, mesaconic acid, glutaconic acid, aconitic acid, fumaric acid, tricarboxy ethylene, and mixtures thereof, preferably maleic acid or maleic anhydride; the monocarboxylic acid monomer is selected from acrylic acid, methacrylic acid, 2-ethylacrylicacid, alpha-chloro-acrylic acid, alpha-cyano acrylic acid, alpha-chloro-acrylic acid, alpha-cyano acrylic acid, beta methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), and mixtures thereof, preferably acrylic acid, methacrylic acid, ethacrylic acid and mixtures thereof; the non-ionic monomer is selected from the group consisting of $C_1$-$C_6$ alkyl esters of (meth)acrylic acid and the alkali or alkaline earth metal or ammonium or tetralkylammonium salts thereof, acrylamide and the $C_1$-$C_6$ alkyl-substituted acrylamides, the N-alkyl-substituted acrylamides and the N-alkanol-substituted acrylamides, the $C_1$-$C_6$ alkyl esters and $C_1$-$C_6$ alkyl half-esters of unsaturated vinylic acids, such as maleic acid and itaconic acid, and $C_1$-$C_6$ alkyl esters of saturated aliphatic monocarboxylic acids, such as acetic acid, propionic acid and valeric acid, preferably methyl (meth)acrylate, mono- and dimethyl maleate, mono- and di-ethyl itaconate, and (meth)allyl acetates, propionates and valerates; and the sulfonated or sulfated monomer consists of one or more ethylenically unsaturated monomers containing a sulfonate functionality, including but not limited to (meth)acrylamido methyl propane sulfonic add, styrene sulfonic add, acrylamido alkyl or aryl sulfonic add, allyl sulfonic add, methallyl sulfonic add, and salts thereof, preferably (meth)acrylamido methyl propane sulfonic add (AMPS) sodium salt. In one embodiment the water soluble polymer is a polymer disclosed in U.S. Pat. No. 7,087,189 and references cited therein, incorporated herein by reference in their entirety, with the addition of a fluorescent monomer as described herein.

In one embodiment the water soluble polymer can further include a naturally derived hydroxy-containing chain transfer agent selected from a monosaccharide, disaccharide, oligosaccharide or polysaccharide, and derivatives of any of the foregoing. Such hydroxy-containing chain transfer agents are described in U.S. Pat. Nos. 7,666,963 and 9,109,068, incorporated herein by reference in its entirety. Other suitable chain transfer agents can include without limitation mercaptans, ferric and cupric salts, bisulfites, and lower secondary alcohols, preferably isopropanol.

All molecular weights in this patent application are weight average molecular weights. The weight average molecular weight of these polymers, apart from any optional naturally derived hydroxy-containing chain transfer agent, is from about 500 atomic mass units (hereinafter "a.m.u.") to about 200,000 a.m.u. Preferably the molecular weight is from about 1000 a.m.u. to about 100,000 a.m.u. Most preferably, the molecular weight is from about 1000 a.m.u. to about 40,000 a.m.u.

Labeling of the water soluble polymer through the use of the fluorescent monomers disclosed herein is achieved by synthesizing the water soluble polymer in the presence of the fluorescent monomer.

The polymerization is generally carried out in an aqueous medium through the copolymerization of fluorescent monomers with one or more water soluble ethylenically unsaturated monomers. The polymers may be prepared by any number of conventional means well known to those skilled in the art including, for instance, such techniques as bulk, emulsion, suspension, precipitation, or preferably solution polymerization.

The polymer compositions are preferably prepared in an aqueous medium in the presence of any initiator or initiator system capable of liberating free radicals under the reaction conditions employed. The free radical initiators are present in an amount ranging from about 0.01% to about 3% by weight based on total monomer weight. In an embodiment, the initiating system is soluble in water to at least 0.1 weight percent at 25° C. Suitable initiators include, but are not limited to, peroxides, azo initiators as well as redox systems, such as tert-butyl hydroperoxide and erythorbic acid, and metal ion based initiating systems. Initiators may also include both inorganic and organic peroxides, such as hydrogen peroxide, benzoyl peroxide, acetyl peroxide, and lauryl peroxide; organic hydroperoxides, such as cumene hydroperoxide and t-butyl hydroperoxide. In an embodiment, the inorganic peroxides, such as sodium persulfate, potassium persulfate and ammonium persulfate, are preferred. In another embodiment, the initiators comprise metal ion based initiating systems including Fe and hydrogen peroxide, as well as Fe in combination with other peroxides. Organic peracids such as peracetic acid can be used. Peroxides and peracids can optionally be activated with reducing agents, such as sodium bisulfite, sodium formaldehyde, or ascorbic acid, transition metals, hydrazine, and the like. A preferred system is the redox system of sodium persulfate and sodium bisulfite. Azo initiators, especially water soluble azo initiators, may also be used. Water soluble azo initiators include, but are not limited to, 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis{2-[1-(2-hydroxyethyl)-2-imidazolin-2-yl]propane}dihydrochloride, 2,2'-Azobis[2-(2-imidazolin-2-yl)propane], 2,2'-Azobis(1-imino-1-pyrrolidino-2-ethylpropane)dihydrochloride, 2,2'-Azobis{2-methyl-N-[1,1-bis(hydroxymethyl)-2-hydroxyethl]propionamide}, 2,2'-Azobis[2-methyl-N-(2-hydroxyethyl)propionamide] and others.

The polymer compositions may be added to the aqueous systems or may be formulated into various water treatment compositions which may then be added to the aqueous systems. In certain aqueous systems where large volumes of water are continuously treated to maintain low levels of deposited matter, the polymers may be used at levels as low as 0.5 ppm (parts per million). The upper limit on the level of polymer used will be dependent upon the particular aqueous system to be treated. For example, when used to disperse particulate matter the polymer may be used at levels ranging from 0.5 ppm to 2,000 ppm. When used to inhibit the formation or deposition of mineral scale the polymer may be used at levels ranging from 0.5 ppm to 100 ppm, preferably from 3 ppm to 20 ppm, more preferably from 5 ppm to 10 ppm.

Once prepared, the water soluble polymers can be incorporated into a water treatment composition comprising about 10-25 wt % of the water soluble polymer and optionally other water treatment chemicals. Such other chemicals include corrosion inhibitors such as orthophosphates, zinc compounds and azoles such as tolyltriazole and benzotriazole. As indicated above, the level of the fluorescent polymer utilized in the water treatment compositions will be determined by the treatment level desired for the particular aqueous system to be treated. Conventional water treatment compositions are known to those skilled in the art and exemplary water treatment compositions are set forth below, in which HEDP is hydroxyethylidene diphosphonic acid and TKPP is tetrapotassium pyrophosphate.

| Formulation 1 | Formulation 2 |
|---|---|
| 11.3% Polymer (40% active) | 11.3% Polymer (40% active) |
| 47.7% Water | 59.6% Water |
| 4.2% HEDP | 4.2% HEDP |
| 10.3% NaOH | 18.4% TKPP |
| 24.5% Sodium Molybdate | 7.2% NaOH |
| 2.0% Tolyltriazole | 2.0% Tolyltriazole |
| pH 13.0 | pH 12.6 |

| Formulation 3 | Formulation 4 |
|---|---|
| 22.6% Polymer (40% active) | 11.3% Polymer (40% active) |
| 51.1% Water | 59.0% Water |
| 8.3% HEDP | 4.2% HEDP |
| 14.0% NaOH | 19.3% NaOH |
| 4.0% Tolyltriazole | 2.0% Tolyltriazole |
|  | 4.2% ZnCl2 |
| pH 12.5 | pH 13.2 |

| Formulation 5 |
|---|
| 25.0% Polymer (40% active) |
| 65.0% Water (soft or DI) |
| 6.0% 2-Phosphonobutane-1,2,4-Tricarboxylic Acid (50% active) |
| 1.0% Muriatic Acid |
| 3.0% Benzotriazole |
| pH 13.0 |

Once created, the fluorescent water soluble polymers can be used as scale inhibitors in any industrial water system where a scale inhibitor is needed.

This disclosure further relates to a method of inhibiting scale in an industrial water system, the method comprising the steps of
 a) providing an industrial water system susceptible to unwanted scaling; and
 b) adding to the water of said industrial water system from about 0.5 ppm to about 2000 ppm of a scale inhibitor, wherein said scale inhibitor comprises a fluorescent polymer composition comprising fluorescent pyranine monomers and non-fluorescent monomers, said fluorescent polymer composition being substantially free of pyranine, said fluorescent pyranine monomers being selected from monomers of formula (IIa)

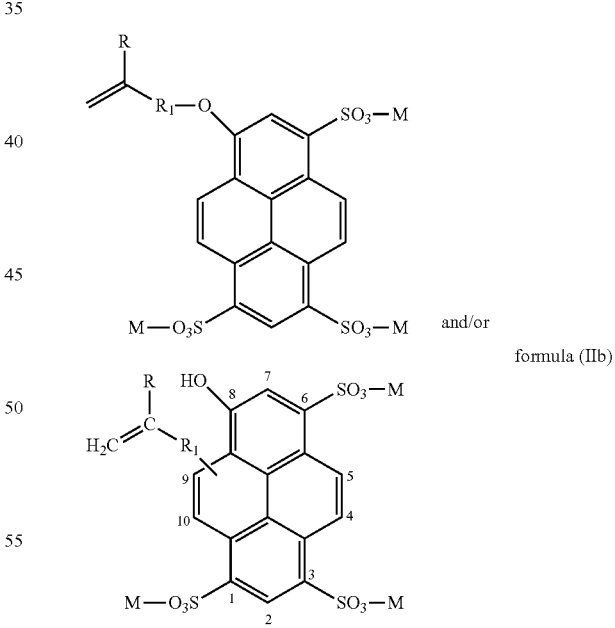

and/or formula (IIb)

wherein
$R_1$ is selected from optionally substituted $C_1$-$C_{10}$alkyl, aryl-$C_2$-$C_{10}$alkyl, —C(O)—, —CH$_2$NH—C(O)—, —C(CH$_3$)$_2$—NH—C(O)—,
R is optionally substituted $C_1$-$C_{10}$alkyl, and
M is selected from the group consisting of hydrogen, sodium, potassium, cesium, rubidium, lithium, ammonium, and tetralkylammonium, wherein the sum of the mole percent of unfunctionalized pyranine compound and the mole percent of unpolymerized pyranine monomer is no more than 5 mole percent of the total pyranine in the polymer composition.

The non-fluorescent monomers are selected from one or more of the group consisting of acrylic add and salts, methacrylic acid and salts, maleic acid and salts, maleic anhydride, acrylamide, crotonic acid and salts; itaconic acid and salts, methacrylamide, 2-acrylamido-2-methylpropanesulfonic acid and salts, sodium (meth)allyl sulfonate, allyloxybenzene sulfonic acid and its salts, polyethylene glycol monomethacrylate, vinyl phosphonic acid and salts, styrene sulfonic acid and salts, vinyl sulfonic add and salts, 3-allyloxy-2-hydroxypropane sulfonic add and salts, N-alkyl (meth)acrylamide, t-butyl (meth)acrylate, N-alkyl (meth) acrylate, N-alkanol-N-alkyl(meth)acrylate, vinyl acetate, 2-Hydroxy N-alkyl(meth)acrylate, alkyl vinyl ether, alkoxyethyl acrylate, N-alkanol (meth)acrylamide, N,N-dialkyl (meth)acrylamide and 1-vinyl-2-pyrrolidinone, sulfomethylacrylamide and sulfoethylacrylamide.

Industrial water systems, include, but are not limited to, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

In addition, the fluorescent water soluble polymers can be used as scale inhibitors in oilfield applications. Scale formation is a major problem in oilfield applications. Subterranean oil recovery operations can involve the injection of an aqueous solution into the oil formation to help move the oil through the formation and to maintain the pressure in the reservoir as fluids are being removed. The injected water, either surface water (lake or river) or seawater (for operations offshore) can contain soluble salts such as sulfates and carbonates. These salts tend to be incompatible with ions already present in the oil-containing reservoir (formation water). The formation water can contain high concentrations of certain ions that are encountered at much lower levels in normal surface water, such as strontium, barium, zinc and calcium. Partially soluble inorganic salts, such as barium sulfate and calcium carbonate, often precipitate from the production water as conditions affecting solubility, such as temperature and pressure, change within the producing well bores and topsides. This is especially prevalent when incompatible waters are encountered such as formation water, seawater, or produced water.

Barium sulfate and strontium sulfate form very hard, very insoluble scales that are difficult to prevent. Barium sulfate or other inorganic supersaturated salts can precipitate onto the formation forming scale, thereby clogging the formation and restricting the recovery of oil from the reservoir. The insoluble salts can also precipitate onto production tubing surfaces and associated extraction equipment, limiting productivity, production efficiency and compromising safety. Certain oil-containing formation waters are known to contain high barium concentrations of 400 ppm, and higher. Since barium sulfate forms a particularly insoluble salt, the solubility of which declines rapidly with temperature, it is difficult to inhibit scale formation and to prevent plugging of the oil formation and topside processes and safety equipment.

Methods of using water soluble polymers as scale control agents in oilfield applications include but are not limited to continuous injection, squeeze treatment, slow release of solid scale inhibitor. These methods are well known in the art and are described in Chapter 3-scale control, Production chemicals for oil and gas industry, CRC press, 2009, pages 75-84.

As stated previously, these fluorescent water soluble polymers function as scale inhibitors. As these water soluble polymers are consumed performing that function, their fluorescent signal will decrease and thus the decrease in the fluorescent signal can be used to indicate that undesired scaling is taking place. Advantageously, the tagged polymer compositions are substantially free of unpolymerized pyranine, which includes both unfunctionalized pyranine and pyranine monomer; if present, the unpolymerized pyranine would emit its own fluorescent signal, so that the decrease in signal from the consumption of the tagged polymer would be difficult or impossible to detect. The water soluble polymer tagged with the fluorescent monomer may be used in the industrial water systems singly or in combination with other polymers, which are not tagged.

When used in an industrial water system, the fluorescent signal of the water soluble polymers can be used to determine how much polymer is present in the industrial water system, as is known in the art.

An advantage of the fluorescent monomers disclosed herein is that in their use in the formation of a tagged polymer, the fluorescent monomer is not significantly affected by other structures in the polymer or by other ingredients in the system. A further advantage of the disclosed water soluble polymers is that the spectral properties, i.e. both excitation and emission of the polymers are in the visible wavelength region, thus allowing the use of solid state instrumentation and potentially minimizing interferences that generally occur in the UV wavelength region.

EXAMPLES

The following examples are intended to be illustrative of the present invention and to teach one of ordinary skill in the art to make and use the invention. These examples are not intended to limit the invention in any way.

The pyranine used in the following examples was Keystone™ Liquid Pyranine sold as an aqueous solution of 19-23% pyranine by Keystone Aniline Corporation, Chicago, Ill. For purposes of calculating completion of reaction it was assumed that the pyranine solutions used contained 23% pyranine.

Methallyl chloride was obtained from Alfa Aesar, Tewksbury, Mass.

NMR measurements were conducted using $^{13}C$ analysis on an Agilent DD2 MR 500 MHz NMR Spectrometer, and in DMSO solvent, unless otherwise indicated.

Liquid chromatography measurements were conducted using a liquid chromatography/ultra-violet/mass spectroscopy procedure as follows:

10 ul of sample was weighed into an auto-sampling vial and diluted with 1.0 ml of water. The diluted sample was analyzed by LC/UV 400 nm/MS with indicated conditions.

| | |
|---|---|
| Column | Poroshell C8 50 mm × 4 mm (Agilent, Santa Clara, CA) |
| Mobile phase | 99% A - 25 mm ammonium acetate |
| | 1% B - Acetonitrile |
| Oven | 40° C. |
| Flow Rate | 0.50 ml/min |
| Injection | 2.0 ul |

The mass spectroscopy trace was used to qualitatively confirm the peak, but quantitation was from the ultraviolet trace only. There was no interference in the area of pyranine.

Example 1: Methallyl Oxy Pyranine Synthesized in Water and Methanol 548.7 g Keystone™ liquid pyranine solution and 100.1 g of methanol were charged to a 1 L multi-neck round bottom flask equipped with mechanical agitator, thermocouple, methallyl chloride dosing line, NaOH 50% dosing line, and condenser. The mixture was heated to 70° C. and upon reaching the reaction temperature slow additions of methallyl chloride and NaOH 50% were begun. The reaction mixture was refluxed at 70-72° C. during the addition. The methallyl chloride was added over 4 hours while the 50% NaOH was added over 6 hr period, for addition rates of about 7 g/hr and 5 g/hr, respectively. After addition of the NaOH, 50% solution was complete, the reaction mixture was held at 70° C. for 2 more hours. The methanol was removed by distillation at 70-75° C. under nitrogen sparging. Approximately 120 g of distillate was removed.

Table 1 summarizes the material balance of the initial reaction mixture.

TABLE 1

Material balance

| Material | Wt (g) | Wt % | EW (g/eq) | moles |
|---|---|---|---|---|
| Pyranine solution (assume 23%) | 548.7 | 78.01 | 2280.00 | 0.241 |
| NaOH, 50% | 25.6 | 3.64 | 80 | 0.320 |
| Methallyl chloride | 29.0 | 4.12 | 90.55 | 0.320 |
| Methanol | 100.1 | 14.23 | — | — |
| Total | 703.4 | 100.0 | | |

Table 2 sets forth the composition of the reaction product after distillation, as determined by NMR.

TABLE 2

Percentage Composition of Example 1 Reaction Product

| | Reaction Product | |
|---|---|---|
| Component | Mole % | Weight % |
| methallyl oxy pyranine | 82.3 | 87.1 |
| methallyl pyranine | 9.8 | 10.3 |
| Unreacted Pyranine | 1.4 | 1.5 |
| Methallyl Alcohol | 3.3 | 0.4 |
| Dimethallyl Ether | 3.2 | 0.7 |

The unfunctionalized pyranine content was 1.4 mol % of the total moles of unfunctionalized pyranine, methallyl oxy pyranine and methallyl pyranine.

Example 2: Methallyl Oxy Pyranine Synthesized in Water and 1-Propanol 548.7 g Keystone™ liquid pyranine solution and 100.1 g of 1-propanol were charged to a 1 L multi-neck round bottom flask equipped with mechanical agitator, thermocouple, methallyl chloride dosing line, NaOH, 50% dosing line, and condenser. The mixture was heated to 70° C. and upon reaching the reaction temperature slow additions of methallyl chloride and NaOH, 50% were begun. The reaction mixture was refluxed at 70-72° C. during the addition. The methallyl chloride was added over 4 hours while the 50% NaOH was added over 6 hr period. After completion of the NaOH, 50% addition, the reaction mixture was held at 70° C. for 2 more hours. No distillation or other isolation steps were performed on the reaction product.

Table 3 summarizes the material balance of the initial reaction mixture.

TABLE 3

Material balance

| Material | Wt (g) | Wt % | EW (g/eq) | moles |
|---|---|---|---|---|
| Pyranine solution (calculated as 23%)* | 548.7 | 78.01 | 2280.00 | 0.241 |
| NaOH, 50% | 25.6 | 3.64 | 80 | 0.320 |
| Methallyl chloride | 29.0 | 4.12 | 90.55 | 0.320 |
| 1-propanol | 100.1 | 14.23 | — | — |
| Total | 703.4 | 100.0 | | |

*Pyranine solution as supplied is 19-23% pyranine

Table 4 sets forth the composition of the reaction product as determined by NMR.

TABLE 4

Composition of Example 2 Reaction product

| | Reaction Product | |
|---|---|---|
| Component | Mole % | Weight % |
| methallyloxy pyranine | 52.2 | 81.5 |
| methallyl pyranine | 6.1 | 9.5 |
| Methallyl Alcohol | 34.8 | 6.8 |
| Dimethallyl Ether | 2.8 | 0.9 |
| 2-methyl-3-propoxyprop-1-ene | 4.2 | 1.3 |

No unfunctionalized pyranine was detected by NMR. The unfunctionalized pyranine content was 0.11 wt % of the final solution as determined by LC. The unfunctionalized pyranine content was 0.55 wt % (0.61 mol %) of the total of pyranine, methallyl oxy pyranine and methallyl pyranine.

Example 3: Methallyl Oxy Pyranine Synthesized in Water and 2-Propanol

Example 2 was repeated, but 2-propanol was used instead of 1-propanol. The unfunctionalized pyranine content was 0.50 wt % (0.55 mol %) of the total of unfunctionalized pyranine, methallyl oxy pyranine and methallyl pyranine, as determined by NMR.

Example 4: Comparative—Monomer Example II of U.S. Pat. No. 6,312,644

A quantity of the Keystone™ pyranine solution was dried in an oven at 60° C. over a 24 hour period to remove the water. Under a nitrogen atmosphere, the dried pyranine (solid, 2.62 g, 5.0 mmol) was added to dry DMSO (25 mL) along with NaOH, 50% (0.48 g, 6.0 mmol) and stirred at room temperature for a 30 minute period. Not all of the pyranine was dissolved after 30 minutes. However, following Monomer Example II of U.S. Pat. No. 6,312,644, allyl chloride (0.4831 g, 6.31 mmol) was added to the mixture in a single addition. The reaction mixture was stirred for a 6-hr period at room temperature. The next day the reaction mixture was filtered through a glass filter into a 100-mL round bottom flask; the solid filtered material was assumed to be sodium chloride. The majority of DMSO was removed by rotary evaporation (80 C, 7 Torr). The residue was washed with 100 mL of acetone for a 3-hr period which caused an insoluble solid to precipitate. The solid was filtered, collected and dried at room temperature to remove residual acetone. Only 1.0 g of solid was collected from the reaction. Analysis of the solid by NMR ($D_2O$ solvent) is reported in Table 5. No alkylation product was detected by NMR.

TABLE 5

Composition of Example 4 Reaction Product

| Component | Example 4 Mole % | Example 4 Weight % |
|---|---|---|
| Allyl oxypyranine | 91.0 | 91.6 |
| Unreacted Pyranine | 9.0 | 8.4 |

It was determined by liquid chromatography that the sample contained unreacted pyranine at a concentration of 80 mg/g, or 8 wt % or 9 mole %.

Example 5: Synthesis of Polymer Containing Methallyl Oxy Pyranine Monomer 247 g of water was added to a round bottom flask. Next, 66.1 g of maleic anhydride was added with stirring. 27 g of 50% sodium hydroxide was then added along with 0.0616 g of ferrous ammonium sulfate hexahydrate. The initial charge was heated to 85° C. A monomer mixture containing 125.3 g of acrylic acid, 11.9 g of methyl methacrylate, 74 g of AMPS 2403 from Lubrizol (50% AMPS) and 22.5 g of the liquid reaction product from Example 2, (which contains 1.88 g of methallyl oxy pyranine, 0.1 mole percent of the monomer mixture) was added over 4 hours. Simultaneously, an initiator solution containing 15.3 g of sodium persulfate, 50.9 g of 35% hydrogen peroxide dissolved in 25 g of water was added over the same period of 4 hours. The reaction mixture was held for one hour at 85° C. The reaction mixture was then cooled down to room temperature and 50.4 g of 50% sodium hydroxide was added. The polymer solution contained approximately 40% polymer solids and a pH of 4.5.

Example 6: Methallyl Oxy Pyranine Synthesized in Water and 1-Propanol, with all Base Added at Start of Reaction Pyranine solution, 19-23% in water (553.9 g, Milikin), 1-propanol (100.0 g) and sodium hydroxide, 50% (25.88 g) were charged to a 1-L multi-neck round bottom flask equipped with mechanical agitator, thermocouple, methallyl chloride dosing line, and condenser. The mixture was heated to 70° C. and upon reaching the reaction temperature a flow of methallyl chloride begun (0.13 mL/min, 247 minutes, 34.71 g) and the reaction mixture refluxed at 70-72° C. during the addition. After completion of the methallyl chloride addition, the mixture was digested for a 4 hr period at 70° C. The reaction mixture was cooled and discharged (700 g). Table 6 summarizes the material balance and Table 7 the analysis of the sample compared to the sample made by co-dosing the sodium hydroxide and methallyl chloride to the pyranine solution.

TABLE 6

Material balance of Example 6

| Material | Wt(g) | Wt % | EW (g/eq) | moles |
|---|---|---|---|---|
| Pyranine solution, 19-23% | 553.9 | 78.07 | 2280.00 | 0.243 |
| NaOH, 50% | 25.9 | 3.65 | 80 | 0.324 |
| Methallyl chloride | 29.7 | 4.18 | 90.55 | 0.328 |
| 1-propanol | 100.0 | 14.09 | — | — |

TABLE 7

NMR analysis of co-dosing process

| Component | Ex. 6 (NaOH added upfront) Weight % | Ex. 6 (NaOH added upfront) Mole % | Ex. 2 (co-dosing) Weight % | Ex. 2 (co-dosing) Mole % |
|---|---|---|---|---|
| methallyl oxy Pyranine | 79.1 | 48.4 | 81.5 | 52.2 |
| Unreacted Pyranine | 1.6 | 1.1 | ND | ND |
| Methallyl Alcohol | 8.0 | 39.0 | 6.8 | 34.8 |
| Dimethallyl Ether | 0.7 | 2.1 | 0.9 | 2.8 |
| methallyl Pyranine | 9.5 | 5.8 | 9.5 | 5.8 |
| 2-methyl-3-propoxyprop-1-ene | 1.2 | 3.6 | 1.3 | 4.2 |

As seen in Table 7, the co-dosing method gives higher amounts of pyranine reaction product along with reducing the amount of unreacted pyranine to below the detection limit of NMR of ~1 mol %. A higher rate of methallyl alcohol formation is likely the cause of the lower conversion for the process in which the NaOH is added upfront. This hypothesis is supported by the higher amount of methallyl alcohol seen in the NMR analysis. The method of Example 2 achieved higher conversion of pyranine to polymerizable monomers than the method of Example 6.

Example 7: Synthesis of Polymer

An initial charge of 248 g deionized water and 66 g of maleic anhydride was added to a 1-liter glass reactor with inlet ports for an agitator, water cooled condenser, thermocouple, and adapters for the addition of monomer and initiator solutions. The reactor contents were heated 85° C. 27 g of 50% sodium hydroxide and 0.0616 g of ferrous ammonium sulfate hexahydrate was added. A mixed monomer solution which consisted of 125.5 g of acrylic acid, 11.9 g of methyl methacrylate, 74.3 g of AMPS 2403 (50% solution of sodium AMPS from Lubrizol) 8.13 g of the monomer solution from Example 2 was fed to the reactor via measured slow-addition with stirring over a period of 4 hours. An initiator solution of 50.9 g of 35% hydrogen peroxide, 15.2 grams sodium persulfate dissolved in 25 grams water was concurrently added, starting at the same time as the monomer solution, for a period of 4 hours. The reaction product was then held at 85° C. for 30 minutes.

Next, 0.36 g of erythorbic acid dissolved in 3 g of water was added. Immediately after that, 0.36 g of tertiary butyl hydroperoxide, 70% solution dissolved in 3 g of water was added. The reaction mixture was then heated at 85° C. for 1 hour. The polymers partially neutralized with 50.4 g of 50% sodium hydroxide. The final reaction mixture was an amber colored solution with a solids of about 40%, and a pH of 4.4.

Example 8: Synthesis of Polymer

An initial charge of 248 g deionized water and 66 g of maleic anhydride was added to a 1-liter glass reactor with inlet ports for an agitator, water cooled condenser, thermocouple, and adapters for the addition of monomer and initiator solutions. The reactor contents were heated 85° C. 27 g of 50% sodium hydroxide and 0.0616 g of ferrous ammonium sulfate hexahydrate was added. A mixed monomer solution which consisted of 125.5 g of acrylic acid, 11.9 g of methyl methacrylate, 74.3 g of AMPS 2403 (50% solution of sodium AMPS from Lubrizol) 22.35 g of the monomer solution from Example 2 was fed to the reactor via measured slow-addition with stirring over a period of 4 hours. An initiator solution of 50.9 g of 35% hydrogen peroxide, 15.2 grams sodium persulfate dissolved in 25 grams water was concurrently added, starting at the same time as the monomer solution, for a period of 4 hours. The reaction product was then held at 85° C. for 30 minutes. Next, 0.36 g of erythorbic acid dissolved in 3 g of water was added. Immediately after that, 0.36 g of tertiary butyl hydroperoxide, 70% solution dissolved in 3 g of water was added. The reaction mixture was then heated at 85° C. for 1 hour. The polymers partially neutralized with 50.4 g of 50% sodium hydroxide. The final reaction mixture was an amber colored solution with a solids of about 40%, and a pH of 4.4.

Example 9: Scale Control

Various water treatment polymers were evaluated for their ability to prevent the precipitation of calcium carbonate in typical cooling water conditions, a property commonly referred to as the threshold inhibition. Solutions were prepared in which the ratio of calcium concentration to alkalinity was 1.000:1.448 to simulate typical conditions in industrial water systems used for cooling. Generally, water wherein the alkalinity is proportionately less will be able to reach higher levels of calcium, and water containing a proportionally greater amount of alkalinity will reach lower levels of calcium. Since cycle of concentration is a general term, one cycle was chosen, in this case, to be that level at which calcium concentrations equaled 100.0 mg/L Ca as $CaCO_3$ (40.0 mg/L as Ca). The complete water conditions at one cycle of concentration (i.e., make-up water conditions) were as follows:

Simulated Make-Up Water Conditions:
100.00 mg/L Ca as $CaCO_3$ (40.0 mg/L as Ca) (one cycle of concentration)
49.20 mg/L Mg as $CaCO_3$ (12.0 mg/L as Mg)
2.88 mg/L Li as $CaCO_3$ (0.4 mg/L Li as Li)
144.80 M Alkalinity (144.0 mg/L as $HCO_3$)
13.40 P Alkalinity (16.0 mg/L as $CO_3$)

In dynamic testing, where the pH is about 8.80, bulk water temperature is around 104° F., flow is approximately 3.0 m/s, and heat transfer is approximately 17,000 BTU/hr/ft$^2$, above average threshold inhibitors can reach anywhere from four to five cycles of concentration with this water before significant calcium carbonate precipitation begins. Average threshold inhibitors may only be able to reach three to four cycles of concentration before precipitating, while below average inhibitors may only reach two to three cycles of concentration before precipitation occurs.

Polymer performance is generally expressed as percent calcium inhibition. This number is calculated by taking the actual soluble calcium concentration at any given cycle, dividing it by the intended soluble calcium concentration for that same given cycle, and then multiplying the result by 100. Resulting percentage amounts that are below 90% calcium inhibition are considered to be indicators of a significant precipitation of calcium carbonate. However, there are two ways in which an inhibitor can react once the threshold limit is reached. Some lose practically all of their calcium carbonate threshold inhibition properties, falling from 90-100% to below 25% threshold inhibition. Others are able to "hold on" better to their inhibition properties, maintaining anywhere from 50% to 80% threshold inhibition.

Testing beyond the threshold limit in order to determine each inhibitor's ability to "hold on" has been found to be a better method of predicting an inhibitor's ability to prevent the formation of calcium carbonate in the dynamic testing units. It also allows for greater differentiation in test results. Therefore, a higher cycle (4.0 cycles) was chosen for this test. At this concentration, above average inhibitors should be expected to give better than 60% threshold inhibition. Poor inhibitors should be expected to give less than 20% threshold inhibition, while average inhibitors should fall somewhere in between.

Materials:
One incubator/shaker, containing a 125 mL flask platform, with 34 flask capacity
34 Screw-cap Erlenmeyer Flasks (125 mL)
1 Brinkmann Dispensette (100 mL)
Deionized Water
Electronic pipette(s) capable of dispensing between 0.0 mL and 2.5 mL
250 Cycle Hardness Solution*
10,000 mg/L treatment solutions, prepared using known active solids of the desired treatment*
10% and 50% solutions of NaOH
250 Cycle Alkalinity Solution*
0.2 μm syringe filters or 0.2 μm filter membranes
34 Volumetric Flasks (100 mL)
Concentrated Nitric Acid

* See solution preparations in next section.

Solution Preparations:
All chemicals used were reagent grade and weighed on an analytical balance to ±0.0005 g of the indicated value. All solutions were made within thirty days of testing. The hardness, alkalinity, and 12% KCl solutions were prepared in a one liter volumetric flask using DI water. The following amounts of chemical were used to prepare these solutions—

250 Cycle Hardness Solution:
10,000 mg/L Ca⇒36.6838 g $CaCl_2·2H_2O$
3,000 mg/L Mg⇒25.0836 g $MgCl_2·6H_2O$
100 mg/L⇒Li 0.6127 g LiCl
250 Cycle Alkalinity Solution:
36,000 mg/L $HCO_3$⇒48.9863 g $NaHCO_3$
4,000 mg/L $CO_3$⇒7.0659 g $Na_2CO_3$
10,000 mg/L Treatment Solutions:
Using percentage of active product in the supplied treatment, 250 mL of a 10,000 mg/L active treatment solution was made up for every treatment tested. The pH of the solutions was adjusted to between 8.70 and 8.90 using 50% and 10% NaOH solutions by adding the weighed polymer into a specimen cup or beaker and filling with DI water to approximately 90 mL. The pH of this solution was then adjusted to approximately 8.70 by first adding the 50% NaOH solution until the pH reached 8.00, and then by using the 10% NaOH until the pH equaled 8.70. The solution was then poured into a 250 mL volumetric flask. The specimen cup or beaker was rinsed with DI water and this water was added to the flask until the final 250 mL was reached. The amount of treatment product to be weighed was calculated as follows:

$$\text{Grams of treatment needed} = \frac{(10{,}000 \text{ mg/L}) (0.25 \text{ L})}{(\text{decimal \% of active treatment}) (1000 \text{ mg})}$$

Test Setup Procedure:

The incubator shaker was turned on and set for a temperature of 50° C. to preheat. 34 screw cap flasks were set out in groups of three to allow for triplicate testing of each treatment, allowing for testing of eleven different treatments. The one remaining flask was used as an untreated blank.

The Brinkmann dispensette was calibrated to deliver 96.6 mL, using DI water, by placing a specimen cup or beaker on an electronic balance and dispensing the water into the container for weighing. The dispensette was adjusted accordingly, until a weight of 96.5-96.7 g DI water was delivered. This weight was recorded, the procedure was repeated for a total of three measurements, and the average determined. Once calibrated, 96.6 mL DI water was dispensed into each flask.

Using a 2.5 mL electric pipette, 1.60 mL of hardness solution was added to each flask to simulate four cycles of make-up water.

Using a 250 μL electronic pipette, 200 μL of desired treatment solution were added to each flask to achieve a 20 mg/L active treatment dosage. A new tip on the electric pipette was used for each treatment solution so cross contamination did not occur.

Using a 2.5 mL electric pipette, 1.60 mL of alkalinity solution was added to each flask to simulate four cycles of make-up water. The addition of alkalinity was done while swirling the flask, so as not to generate premature scale formation from high alkalinity concentration pooling at the addition site.

One "blank" solution was prepared in the exact same manner as the above treated solutions, except DI water was added in place of the treatment solution.

All 34 flasks uncapped were placed onto the shaker platform and the door closed. The shaker was run at 250 rpm and 50° C. for 17 hours.

A "total" solution was prepared in the exact same manner as the above treated solutions were prepared, except that DI water was used in place of both the treatment solution and alkalinity solution. This solution was capped and left overnight outside the shaker.

Test Analysis Procedure:

Once 17 hours had passed, the 34 flasks were removed from the shaker and allowed to cool for one hour. Each flask solution was filtered through a 0.2 μm filter membrane. The filtrate was analyzed directly for lithium, calcium, and magnesium concentrations by either an Inductively Couple Plasma (ICP) Optical Emission System or Flame Atomic Absorption (AA) system. The "total" solution was analyzed in the same manner.

Calculations of Results:

Once the lithium, calcium, and magnesium concentrations were known in all 34 shaker samples and in the "total" solution, the percent inhibition was calculated for each treatment. The lithium was used as a tracer of evaporation in each flask (typically about ten percent of the original volume). The lithium concentration found in the "total" solution was assumed to be the starting concentration in all 34 flasks. The concentrations of lithium in the 34 shaker samples were each divided by the lithium concentration found in the "total" sample. These results provided the multiplying factor for increases in concentration, due to evaporation. The calcium and magnesium concentrations found in the "total" solution were also assumed to be the starting concentrations in all 34 flasks. By multiplying these concentrations by each calculated evaporation factor for each shaker sample, the final intended calcium and magnesium concentration for each shaker sample was determined. By subtracting the calcium and magnesium concentrations of the "blank" from both the actual and intended concentrations of calcium and magnesium, then dividing the resulting actual concentration by the resulting intended concentration and multiplying by 100, the percent inhibition for each treated sample was calculated. The triplicate treatments were averaged to provide more accurate results.

Example:

"Total" concentration analysis results:

Li=1.61 mg/L

Ca=158.0 mg/L

Mg=50.0 mg/L

"Blank" concentration analysis results:

Li=1.78 mg/L

Ca=4.1 mg/L

Mg=49.1 mg/L

Shaker sample concentration analysis results:

Li=1.78 mg/L

Ca=150.0 mg/L

Mg=54.0 mg/L

By taking the Li concentration from the shaker sample and dividing by the Li concentration in the "total" sample, the evaporation factor was determined as—

$$\Rightarrow 1.78 \text{ mg/L}/1.61 \text{ mg/L} = 1.11$$

By multiplying the Ca and Mg concentrations in the "total" sample by this factor, the final intended concentrations of Ca and Mg in the shaker sample were determined as—

$$\text{Ca} \Rightarrow 1.11 \times 158.0 \text{ mg/L} = 175.4 \text{ mg/L Ca}$$

$$\text{Mg} \Rightarrow 1.11 \times 50.0 \text{ mg/L} = 55.5 \text{ mg/L Mg}$$

Finally, by subtracting the calcium and magnesium concentrations of the "blank" from both the actual and intended concentrations of calcium and magnesium, then dividing the resulting actual concentrations of Ca and Mg in the shaker sample by the resulting final intended concentrations and multiplying by 100, the percent threshold inhibition of calcium and magnesium was calculated as—

$$\text{Ca} \Rightarrow ((150.0 \text{ mg/L} - 4.1 \text{ mg/L})/(175.4 \text{ mg/L} - 4.1 \text{ mg/L})) \times 100 = 85.2\% \text{ Ca inhibition}$$

$$\text{Mg} \Rightarrow ((54.0 \text{ mg/L} - 49.1 \text{ mg/L})/(55.5 \text{ mg/L} - 49.1 \text{ mg/L})) \times 100 = 76.6\% \text{ Mg inhibition}$$

The polymers of Example 7 and 8 were tested according to the procedure outlined above.

TABLE 8

| | percent calcium carbonate inhibition | | | |
|---|---|---|---|---|
| Polymer | % inhibition at 2 ppm | % inhibition at 3 ppm | % inhibition at 4 ppm | % inhibition at 5 ppm |
| Example 7 | 61 | 87 | 92 | |
| Example 8 | | 87 | 99 | 100 |
| Polymer of Example 7 without fluorescent tag | 56 | 75 | 94 | 100 |

In the test above, anything above 80% inhibition is considered acceptable. These data in Table 8 indicate that the carbonate inhibition performance of the polymer is the same with the fluorescent tag as it is without the tag, indicating that the presence of the tag does not interfere with the primary purpose of the polymer which is scale minimization.

The specific examples herein disclosed are to be considered as being primarily illustrative. Various changes beyond those described will, no doubt, occur to those skilled in the art; and such changes are to be understood as forming a part of this invention insofar as they fall within the spirit and scope of the appended claims.

What is claimed is:

1. A method of making a composition comprising a functionalized pyranine monomer, the method comprising the steps of
   providing a starting amount of pyranine in an aqueous solvent system,
   adding an amount of base to the aqueous solvent system,
   dosing to the aqueous solvent system an amount of a polymerizable functionalizing agent to form a reaction mixture, thereby initiating the reaction of the pyranine with the functionalizing agent to functionalize the pyranine molecule with a polymerizable functional group, and
   maintaining the dosing of the functionalizing agent to the reaction mixture during the reaction of the pyranine with the functionalizing agent until the amount of functionalizing agent dosed to the system exceeds the starting amount of pyranine on a molar basis;
   wherein said composition once made comprises less than 5 mol % unfunctionalized pyranine, based on the total amount of unfunctionalized pyranine and functionalized pyranine.

2. The method of claim 1 wherein the base is added to the solvent system prior to the addition of the functionalizing agent.

3. The method of claim 1 wherein the base and the functionalizing agent are simultaneously dosed to the aqueous solvent system, wherein the dosing of both the functionalizing agent and the base is maintained during the reaction of the pyranine with the functionalizing agent until the amount of functionalizing agent dosed to the system exceeds the starting amount of pyranine on a molar basis.

4. The method of claim 3 wherein the dosing of base to the reaction mixture is continued after the addition of the functionalizing agent is complete and during the continued reaction of the pyranine with the functionalizing agent.

5. The method of claim 3 wherein the base is dosed to the reaction mixture at a rate no faster than the rate of dosage of the functionalizing agent, based on the total dosage amount of base.

6. The method of claim 1 wherein said aqueous solvent system further comprises a water-soluble organic co-solvent.

7. The method of claim 6 wherein the ratio of water to total organic co-solvent on a volume:volume basis is in the range of 20:1-1:20.

8. The method of claim 6 wherein said water-soluble organic co-solvent is selected from the group consisting of $C_1$-$C_6$ alcohols.

9. The method of claim 1 wherein said functionalizing agent is a compound of the formula (I)

$$R-C(=CH_2)-R_1-X \qquad (I),$$

where
$R_1$ is selected from —$C_1$-$C_{10}$alkyl-, -aryl-$C_1$-$C_{10}$alkyl-, —C(O)—, —$CH_2$NH—C(O)—, —$C(CH_3)_2$—NH—C(O)—, any of which may be substituted or unsubstituted;
R is H or unsubstituted or substituted —$C_1$-$C_{10}$alkyl-; and
X is a leaving group.

10. The method of claim 9 wherein R is a methyl group, $R_1$ is $C_1$-$C_{10}$ alkyl, and said monomer composition comprises a compound selected from the group consisting of compounds of formula (III):

(III)

[Chemical structure: pyrene with $MO_3S$, $MO_3S$, $SO_3M$ substituents and an O—[CH$_2$—C(CH$_3$)=CH$_2$]$_n$ group]

wherein M is selected from the group consisting of hydrogen, sodium, potassium, cesium, rubidium, lithium, ammonium, and tetralkylammonium, and
n is an integer from 1-10.

11. The method of claim 1 wherein said monomer composition comprises a compound of formula (IIa)

(IIa)

[Chemical structure: pyrene with $R_1$—O, $SO_3$—M, $M$—$O_3S$, $SO_3$—M substituents, and vinyl R group]

wherein M is selected from the group consisting of hydrogen, sodium, potassium, cesium, rubidium, lithium, ammonium and tetralkylammonium;
$R_1$ is selected from —$C_1$-$C_{10}$alkyl-, -aryl-$C_1$-$C_{10}$alkyl-, —C(O)—, —$CH_2$NH—C(O)—, —$C(CH_3)_2$—NH—C(O)—, any of which may be substituted or unsubstituted; and
R is H or unsubstituted or substituted —$C_1$-$C_{10}$alkyl-.

12. The method of claim 1, wherein said monomer composition further comprises a compound of formula (IIb)

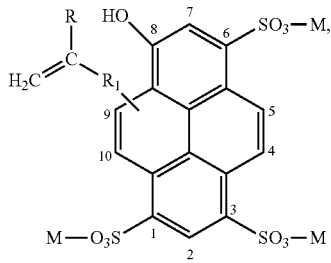

formula (IIb)

wherein M is selected from the group consisting of hydrogen, sodium; potassium cesium, rubidium, lithium, ammonium, and tetralkylammonium;

$R_1$ is selected from —$C_1$-$C_{10}$alkyl-, -aryl-$C_1$-$C_{10}$alkyl-, —C(O)—, —$CH_2$NH—C($CH_3$)$_2$—NH—C(O)—, any of which may be substituted or unsubstituted; and R is H unsubstituted or substituted —$C_1$-$C_{10}$alkyl-.

13. The method of claim 1 wherein said monomer composition further comprises an alcohol of the formula R—C(=$CH_2$)—$R_1$—OH.

14. The method of claim 1 wherein said monomer composition comprises one or more monomers selected form the group consisting of 8-(methallyloxy)-1,3,6-pyrene trisulfonic acid, methallyl-8-(hydroxy)-1,3,6-pyrene trisulfonic acid, 8-(allyloxy)-1,3,6-pyrene trisulfonic acid, vinyl benzyl-8-(hydroxy)-1,3,6-pyrene trisulfonic acid, allyl-8-(hydroxy)-1,3,6-pyrene trisulfonic acid, 2-(methallyl)-1,3,6-pyrene trisulfonic acid, 4-(methallyl)-1,3,6-pyrene trisulfonic acid, 5-(methallyl)-1,3,6-pyrene trisulfonic acid, 7-(methallyl)-1,3,6-pyrene trisulfonic acid; 9-(methallyl)-1,3,6-pyrene trisulfonic acid; 10-(methallyl)-1,3,6-pyrene trisulfonic acid; 2-(allyl)-1,3,6-pyrene trisulfonic acid, 4-(allyl)-1,3,6-pyrene trisulfonic acid, 5-(allyl)-1,3,6-pyrene trisulfonic acid, 7-(allyl)-1,3,6-pyrene trisulfonic acid; 9-(allyl)-1,3,6-pyrene trisulfonic acid; 10-(allyl)-1,3,6-pyrene trisulfonic acid, 2-vinyl benzyl-1,3,6-pyrene trisulfonic acid, 4-vinyl benzyl-1,3,6-pyrene trisulfonic acid, 5-vinyl benzyl-1,3,6-pyrene trisulfonic acid, 7-vinyl benzyl-1,3,6-pyrene trisulfonic acid, 9-vinyl benzyl-1,3,6-pyrene trisulfonic acid, 10 benzyl-1,3,6-pyrene trisulfonic acid; 8-(3-vinyl benzyloxy)-1,3,6-pyrene trisulfonic acid; 8-(4-vinyl benzyloxy)-1,3,6-pyrene trisulfonic acid; and the sodium, potassium, cesium, rubidium, lithium, ammonium, and tetralkylammonium salts thereof of any of the foregoing.

15. A polymer composition comprising a water soluble polymer polymerized from a mixture of monomers comprising a monomer of formula (IIa):

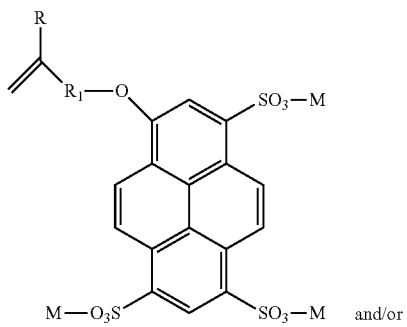

(IIa)

-continued

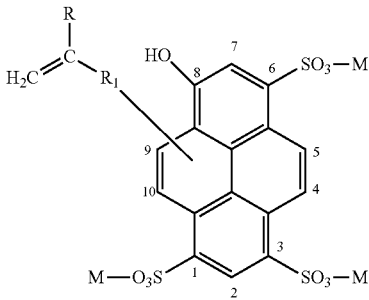

formula (IIb)

wherein M is selected from the group consisting of hydrogen, sodium, potassium, cesium, rubidium, lithium, ammonium, and tetralkylammonium, and $R_1$ is selected from optionally substituted —$C_1$-$C_{10}$alkyl-, -aryl-$C_2$-$C_{10}$alkyl-, —C(O)—, —$CH_2$NH—C(O)—, and —C($CH_3$)$_2$—NH—C(O)—, and R is H or optionally substituted $C_1$-$C_{10}$alkyl-;

wherein the sum of the mole percent of unfunctionalized pyranine compound and the mole percent of unpolymerized pyranine monomer is less than 5 mole percent of the total pyranine in the polymer composition.

16. The polymer composition of claim 15 wherein said water-soluble polymer further comprises one or more monomers selected from the group consisting of acrylic acid and salts, methacrylic acid and salts, maleic acid and salts, maleic anhydride, acrylamide, crotonic acid and salts; itaconic acid and salts, methacrylamide, 2-acrylamido-2-methylpropanesulfonic acid and salts, sodium (meth)allyl sulfonate, allyloxybenzene sulfonic acid and its salts, polyethylene glycol monomethacrylate, vinyl phosphonic acid and salts, styrene sulfonic acid and salts, vinyl sulfonic acid and salts, 3-allyloxy-2-hydroxypropane sulfonic acid and salts, N-alkyl (meth)acrylamide, t-butyl (meth)acrylate, N-alkyl (meth)acrylate, N-alkanol-N-alkyl(meth)acrylate, vinyl acetate, 2-Hydroxy N-alkyl(meth)acrylate, alkyl vinyl ether, alkoxyethyl acrylate, N-alkanol (meth)acrylamide, N,N-dialkyl(meth)acrylamide and 1-vinyl-2-pyrrolidinone sulfomethylacrylamide and sulfoethylacrylamide.

17. The polymer composition of claim 15 further comprising an alcohol of the formula R—C(=$CH_2$)—$R_1$—OH.

18. A composition comprising a functionalized pyranine of formula (IIa)

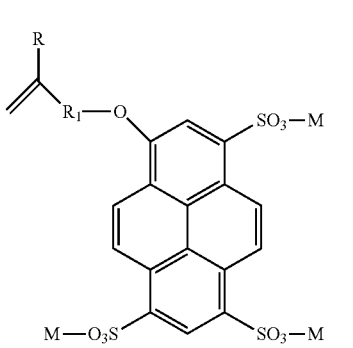

(IIa)

and/or

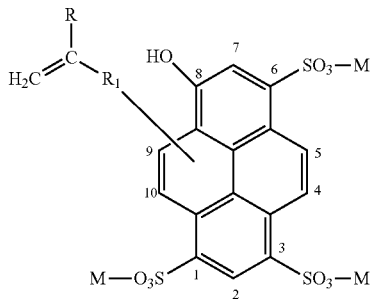

(IIb)

wherein $R_1$ is selected from optionally substituted $C_1$-$C_{10}$alkyl, aryl-$C_2$-$C_{10}$alkyl, —C(O)—, —CH$_2$NH—C(O)—, —C(CH$_3$)$_2$—NH—C(O)—, R is optionally substituted $C_1$-$C_{10}$alkyl, and M is selected from the group consisting of hydrogen, sodium, potassium, cesium, rubidium, lithium, ammonium, and tetralkylammonium, wherein said composition comprises less than 5 mol % unfunctionalized pyranine, based on the total amount of unfunctionalized pyranine and functionalized pyranine.

19. The composition of claim 18 wherein R is methyl and $R_1$ is methylene.

20. A method of inhibiting scale in an industrial water system comprising the steps of a) providing an industrial water system susceptible to unwanted scaling; and b) adding to the water of said industrial water system from about 1 ppm to about 30 ppm of a scale inhibitor, wherein said scale inhibitor comprises a fluorescent polymer composition comprising fluorescent pyranine monomers and non-fluorescent monomers, said fluorescent polymer composition being substantially free of pyranine, said fluorescent pyranine monomers being selected from monomers of formula (IIa)

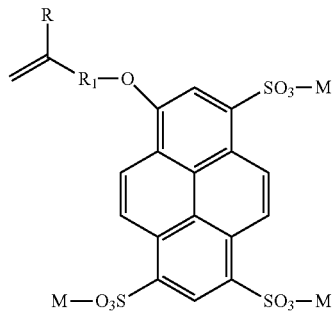

(IIa)

and/or formula (IIb)

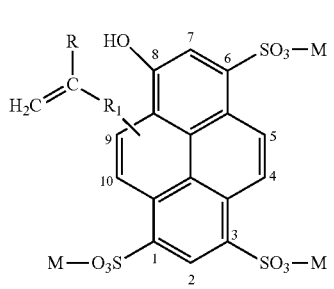

wherein $R_1$ is selected from optionally substituted $C_1$-$C_{10}$alkyl, aryl-$C_2$-$C_{10}$alkyl, —C(O)—, —CH$_2$NH—C(O)—, —C(CH$_3$)$_2$—NH—C(O)—, R is optionally substituted $C_1$-$C_{10}$alkyl, and M is selected from the group consisting of hydrogen, sodium, potassium, cesium, rubidium, lithium, ammonium, and tetralkylammonium, and wherein said non-fluorescent monomers are selected from one or more of the group consisting of acrylic acid and salts, methacrylic acid and salts, maleic acid and salts, maleic anhydride, acrylamide, crotonic acid and salts; itaconic acid and salts, methacrylamide, 2-acrylamido-2-methylpropanesulfonic acid and salts, sodium (meth)allyl sulfonate, allyloxybenzene sulfonic acid and its salts, polyethylene glycol monomethacrylate, vinyl phosphoric acid and salts, styrene sulfonic acid and salts, vinyl sulfonic acid and salts, 3-allyloxy-2-hydroxypropane sulfonic acid and salts, N-alkyl (meth)acrylamide, t-butyl (meth)acrylate, N-alkyl (meth)acrylate, N-alkanol-N-alkyl(meth)acrylate, vinyl acetate, 2-Hydroxy N-alkyl(meth)acrylate, alkyl vinyl ether, alkoxyethyl acrylate, N-alkanol (meth)acrylamide, N,N-dialkyl(meth)acrylamide and 1-vinyl-2-pyrrolidinone; sulfomethylacrylamide and sulfoethylacrylamide.

* * * * *